US008187001B2

(12) United States Patent
Navarro

(10) Patent No.: US 8,187,001 B2
(45) Date of Patent: May 29, 2012

(54) APPARATUS AND METHOD FOR REMOVING ENAMEL FROM A PERSON'S TOOTH

(76) Inventor: Carlos F. Navarro, Dallas, TX (US)

( * ) Notice: Subject to any disclaimer, the term of this patent is extended or adjusted under 35 U.S.C. 154(b) by 0 days.

(21) Appl. No.: 12/838,123

(22) Filed: Jul. 16, 2010

(65) Prior Publication Data

US 2010/0279252 A1    Nov. 4, 2010

Related U.S. Application Data

(63) Continuation of application No. 12/354,107, filed on Jan. 15, 2009, now Pat. No. 7,758,343.

(51) Int. Cl.
*A61C 5/00* (2006.01)
(52) U.S. Cl. .......................... 433/215; 433/125; 433/142
(58) Field of Classification Search .................. 433/125, 433/141, 142, 166, 215; 451/524, 525; 24/453, 24/706, 706.2, 706.5, 707.9, 710, 711.1; 132/322, 323; 606/176, 177, 178
See application file for complete search history.

(56) References Cited

U.S. PATENT DOCUMENTS

| | | |
|---|---|---|
| 3,624,908 A | 12/1971 | Ricketts et al. |
| 4,109,384 A | 8/1978 | Dorian |
| 4,270,556 A | 6/1981 | McAllister |
| 4,483,676 A | 11/1984 | Thierman |
| 4,505,678 A | 3/1985 | Andersson |
| 4,563,152 A | 1/1986 | McClure |
| 4,830,615 A | 5/1989 | Goldstein et al. |
| 4,976,625 A | 12/1990 | Weissman |
| 5,040,977 A | 8/1991 | Weissman |
| 5,476,381 A | 12/1995 | Dragan |
| 5,505,617 A | 4/1996 | Skeppmark et al. |
| 5,613,300 A | 3/1997 | Schmidt |
| 6,247,931 B1 | 6/2001 | Postal et al. |

(Continued)

FOREIGN PATENT DOCUMENTS

DE        3415450 A1    10/1984

(Continued)

OTHER PUBLICATIONS

PCT/US05/32415, Notification of Transmittal of the International Search Report and the Written Opinion of the International Searching Authority, or the Declaration, 6 pages, Mailed Sep. 6, 2006.

(Continued)

*Primary Examiner* — Cris L Rodriguez
*Assistant Examiner* — Eric Rosen
(74) *Attorney, Agent, or Firm* — Baker Botts L.L.P.

(57) ABSTRACT

According to one embodiment, an apparatus for removing enamel from a person's tooth includes a blade portion and a handle portion. The blade portion includes an abrasive surface adapted to remove enamel from the tooth in response to reciprocating movement of the abrasive surface against the enamel. The handle portion is coupled to the blade portion and includes first and second regions, the first region is proximal and the second region is distal to the blade portion. The first region includes a substantially solid cross-section with a substantially circular perimeter. The second region includes a substantially solid cross-section with at least a substantially semi-circular perimeter, the solid cross-section defining a notched region. The apparatus is adapted to be inserted via a pressure fit into a corresponding opening in a driver mechanism adapted to drive reciprocating movement of the blade portion and the abrasive surface.

22 Claims, 6 Drawing Sheets

U.S. PATENT DOCUMENTS

| | | |
|---|---|---|
| 6,508,649 B2 | 1/2003 | Gratz |
| 6,780,013 B2 | 8/2004 | Kubein-Messenburg et al. |
| 6,925,719 B2 | 8/2005 | Callne |
| 7,131,840 B2 | 11/2006 | Constantino |
| 7,322,822 B2 | 1/2008 | Navarro |
| 7,348,046 B2 | 3/2008 | Liedloff et al. |
| 7,758,343 B1 * | 7/2010 | Navarro ........................ 433/142 |
| 2003/0022131 A1 | 1/2003 | Kangasniemi et al. |
| 2003/0228554 A1 | 12/2003 | Brown, Jr. |
| 2004/0091839 A1 | 5/2004 | Fischer |
| 2005/0058963 A1 | 3/2005 | Stockstill |
| 2005/0115085 A1 | 6/2005 | Callne |
| 2006/0057540 A1 | 3/2006 | Navarro |
| 2006/0063131 A1 | 3/2006 | Kim |
| 2008/0131839 A1 | 6/2008 | Navarro |
| 2010/0178633 A1 | 7/2010 | Navarro |

FOREIGN PATENT DOCUMENTS

| | | |
|---|---|---|
| WO | WO 2006/031728 A2 | 3/2006 |
| WO | WO 2006/031728 A3 | 3/2006 |

OTHER PUBLICATIONS

PCT/US2005/032415, Notification Concerning Transmittal of International Preliminary Report on Patentability (Chapter I of the Patent Cooperation Treaty); 5 pages, Mailed Mar. 22, 2007.

PCT/US2009/068039, Notification of Transmittal of the International Search Report and the Written Opinion of the International Searching Authority, or the Declaration, 16 pages, Mailed Apr. 8, 2010.

Supplementary European Search Report; Application No. EP 06 79 6519; 6 pages, Jan. 16, 2009.

Carlos F. Navarro; *"Apparatus and Method for Removing Enamel From a Person's Tooth;"* U.S. Appl. No. 11/225,485; 22 pages, Filed Sep. 13, 2005.

Carlos F. Navarro; *"Apparatus and Method for Removing Enamel From a Person's Tooth;"* Patent Application Serial #US05/32415; 39 pages, Filed Sep. 13, 2005.

Carlos F. Navarro; *"Apparatus and Method for Removing Enamel From a Person's Tooth;"* U.S. Appl. No. 12/011,548; 21 pages, Filed Jan. 28, 2008.

* cited by examiner

APPARATUS AND METHOD FOR REMOVING ENAMEL FROM A PERSON'S TOOTH

RELATED APPLICATIONS

This application is a continuation of U.S. patent application Ser. No. 12/354,107 filed Jan. 15, 2009 now U.S. Pat. No. 7,758,343 by Carlos F. Navarro entitled Apparatus and Method for Removing Enamel From a Person's Tooth.

TECHNICAL FIELD

This invention relates generally to dentistry and orthodontics and in particular to an apparatus and method for removing enamel from a person's tooth.

BACKGROUND

Many people experience adverse conditions resulting from the overcrowding of teeth associated with malocclusion. To avoid the need for one or more tooth extractions, such conditions have been treated effectively by removing enamel from one or more teeth in the person's mouth to create space or additional space. Interproximal Enamel Reduction (IER) is the clinical act of removing part of the enamel from an interproximal contact area of a person's tooth. To perform IER, an orthodontist or other clinical professional manually or mechanically files down the interproximal contact area of the tooth with a metallic strip or disk. Typically, over seven millimeters of space may be created between teeth in a person's upper arch, and over five millimeters of space may be created between teeth in a person's lower arch. In addition to creating space for orthodontic and other treatments, IER may be used to alter the size and shape of a person's teeth. Accordingly, IER often contributes to an improved finishing of orthodontic treatment and dental aesthetics. Because debris from the IER procedure accumulates around the interproximal contact area, the procedure must be interrupted and the interproximal contact area cleaned periodically during the procedure, adding to the length and cost of the procedure. Additionally, tools used for IER are typically constructed from multiple pieces of metal coupled together using welds, rivets, or other means and can be expensive. For economic reasons, these tools typically must be reused a number of times and therefore must be thoroughly cleaned and sterilized between IER procedures, further increasing costs associated with these procedures. Such tools are also typically constructed using molded sheet metal, which results in poor structural integrity, negatively impacting their ability to couple to an associated driver mechanism and reducing their useful life.

OVERVIEW

The apparatus and method of the present invention may reduce or eliminate certain problems and disadvantages associated with previous dental devices.

According to one embodiment, an apparatus for removing enamel from a person's tooth includes a blade portion and a handle portion. The blade portion includes an abrasive surface adapted to remove enamel from the tooth in response to reciprocating movement of the abrasive surface against the enamel. The handle portion is coupled to the blade portion and includes first and second regions, the first region is proximal and the second region is distal to the blade portion. The first region includes a substantially solid cross-section with a substantially circular perimeter. The second region includes a substantially solid cross-section with at least a substantially semi-circular perimeter, the solid cross-section defining a notched region. The apparatus is adapted to be inserted via a pressure fit into a corresponding opening in a driver mechanism adapted to drive reciprocating movement of the blade portion and the abrasive surface.

Particular embodiments of the present invention may provide one or more technical advantages. Various embodiments of the present invention provide an apparatus or method for removing enamel from one or more of a person's teeth. The removal of enamel from one or both of two adjacent teeth may create space, or additional space, between the adjacent teeth. Thus, an IER procedure may be performed to prevent or treat the overcrowding of teeth associated with malocclusion and avoid the need for one or more tooth extractions. Additionally or alternatively, an IER procedure may be used to recontour or otherwise alter the size and shape of one or more of the person's teeth to provide a more aesthetically pleasing result.

In certain embodiments, the apparatus may include a frame with a blade portion having an abrasive surface and a tang portion, preferably metal, that provides strength and rigidity and is unlikely to break or otherwise fail during use. In certain embodiments, portions of the apparatus, including at least the tang portion, are enveloped or otherwise covered by a body, which may be made of plastic, polymer, or composite and may also be integrally-formed. In certain embodiments, the resulting handle may be manually gripped by an orthodontist or other clinical professional when using the apparatus to remove enamel from a person's tooth. In certain embodiments, the apparatus is lightweight and may be easily positioned and manipulated by the clinical professional. In certain embodiments, a driver mechanism may be used in cooperation with the frame to drive reciprocal motion of the abrasive surface of the blade portion of the frame against the enamel of a person's tooth. In certain embodiments, one or more apertures formed through the blade portion of the frame channel debris away from the interproximal contact area as an TER procedure is being performed. As a result, bits of removed enamel, saliva, blood and any liquids, chemicals, or pastes used in the IER procedure and present at the interproximal contact area may be channeled away from the tooth through the one or more apertures and the area kept cleaner and visibly unobstructed during the procedure, reducing or eliminating the need to interrupt the procedure to clean the interproximal contact area. In certain embodiments, the apparatus may be inexpensively mass manufactured such that it is economically practical to dispose of the apparatus after a single use, eliminating the need for cleaning and sterilization between uses. In certain embodiments, the handle contains at least two regions, the first with a substantially solid cross-section and the second with at least a semi-circular cross-section that defines a notched region, and is adapted to be inserted via a pressure fit into a corresponding opening in a driver mechanism that is adapted to drive reciprocating movement of the blade portion to provide the reciprocating movement of the abrasive surface. Certain embodiments may utilize materials with advantageous properties, including advantageous stiffness, strength, durability, stability, and/or chemical resistance.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which.

DESCRIPTION OF EXAMPLE EMBODIMENTS

According to the present invention, an apparatus and method are provided for removing enamel from one or more of a person's teeth. The removal of enamel from one or both of two adjacent teeth may create space, or additional space, between the adjacent teeth. Thus, an IER procedure may be performed to prevent or treat the overcrowding of teeth associated with malocclusion and avoid the need for one or more tooth extractions. Additionally or alternatively, an IER procedure may be used to recontour or otherwise alter the size and shape of one or more of the person's teeth to provide a more aesthetically pleasing result.

Figure 1A:
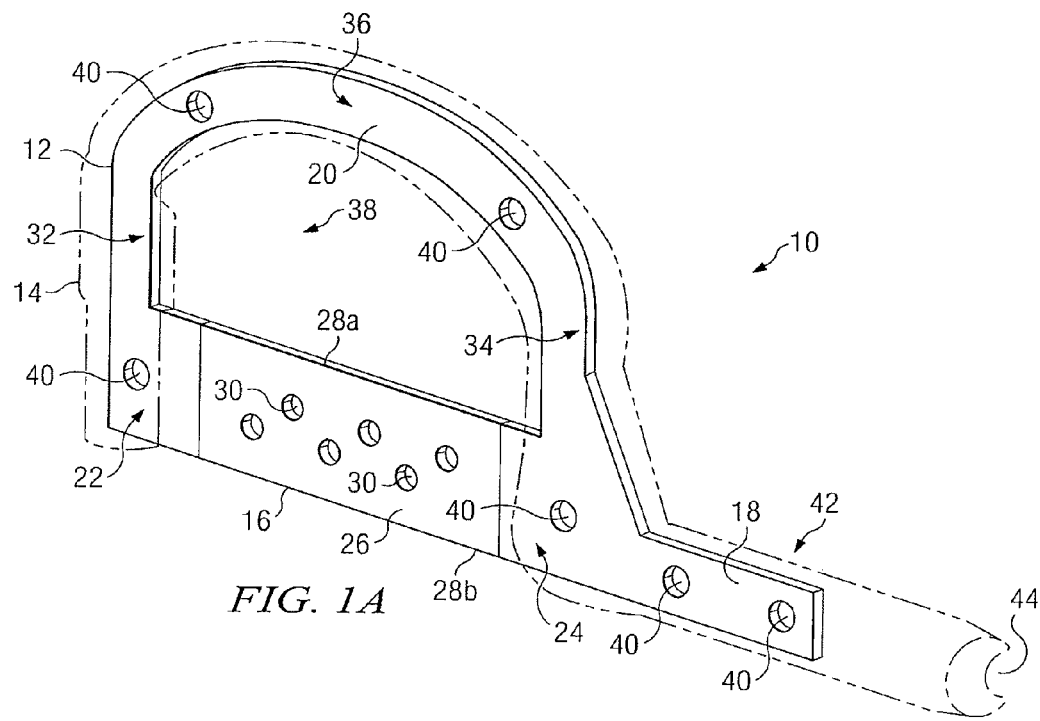
FIG. 1A provides a cut-away view of an example apparatus for removing enamel from a person's tooth.

FIG. 1A illustrates an example apparatus 10 for removing enamel from a person's tooth. Apparatus 10 includes a frame 12 and a body 14. In certain embodiments, frame 12 is a one-piece frame, integrally-formed from a single piece of material. Frame 12 may be made of steel or another metal. Body 14 is formed around frame 12 to envelop or otherwise cover appropriate portions of frame 12. In certain embodiments, body 14 may be a one-piece body integrally-formed of plastic or another suitable material. In particular embodiments, body 14 may be formed of a thermoplastic material, such as for example a composite thermoplastic material. Apparatus 10 may be used to remove enamel from a person's tooth. For example, apparatus 10 may be used to remove enamel from one or both of two adjacent teeth in an IER procedure to create space, or additional space, between the adjacent teeth to prevent or treat overcrowding associated with malocclusion. As another example, apparatus 10 may be used to remove enamel from a tooth in an IER or other procedure to recontour the tooth to provide a more aesthetically pleasing shape. Accordingly, the recontouring of a tooth using apparatus 10 may contribute to an improved finish of orthodontic treatment. After portions of the enamel are removed at an interproximal contact area, the teeth may be polished and a protective treatment applied. The present invention contemplates any appropriate use of apparatus 10 according to particular needs.

In certain embodiments, frame 12 includes a blade portion 16, a tang portion 18, and a stabilizer portion 20. Blade portion 16 extends in a first direction from a first end 22 to a second end 24. Blade portion 16 includes one or more abrasive surfaces 26 adapted to remove enamel from a person's tooth when an abrasive surface 26 of blade portion 16 is repeatedly moved over, through, or otherwise against the enamel of the tooth. For example, abrasive surface 26 may be repeatedly advanced in generally opposing directions with respect to the person's tooth in a manner that causes abrasive surface 26 to gradually remove enamel from the tooth. Such movement is referred to herein as "reciprocating" movement. In certain embodiments, abrasive surface 26 may extend between two edges 28 of blade portion 16 and may be used to "file" or otherwise remove enamel from the person's tooth. In certain other embodiments, instead or in addition, abrasive surface 26 may lie along edge 28b of blade portion 16 and may be used to "saw" or otherwise remove enamel from the tooth.

In certain embodiments, blade portion 16 includes one or more apertures 30 for channeling debris away from the tooth. For example, apertures 30 may comprise substantially circular openings. As blade portion 16 is advanced against the tooth and enamel is gradually removed, the IER procedure may result in the accumulation of debris in and around the interproximal contact area. The accumulated debris may include, for example, bits of removed enamel, saliva, blood and any liquids, chemicals, or pastes used in the IER procedure. Apertures 30 of blade portion 16 may act to channel such debris away from the interproximal contact area such that abrasive surface 26 remains against the interproximal contact area for more accurate enamel removal. Additionally, the patient's mouth may be kept cleaner as the IER procedure is being performed, without undue interruption.

As described above, in certain embodiments frame 12 also includes tang portion 18 and stabilizer portion 20. Tang portion 18 extends from second end 24 of blade portion 16 in generally the same direction as abrasive surface 26. Stabilizer portion 20 operates to stabilize apparatus 10 during use. Although desirable for stability, the present invention contemplates apparatus 10 lacking stabilizer portion 20. In certain embodiments, stabilizer portion 20 is substantially U-shaped and includes a first portion 32, a second portion 34, and a third portion 36. First portion 32 may extend from first end 22 of blade portion 16 in a first direction that is generally perpendicular to the direction of abrasive surface 26. Second portion 34 of stabilizer portion 20 may extend from second end 24 of blade portion 16 in a second direction that is also generally perpendicular the direction of abrasive surface 26. Third portion 36 extends between and couples first portion 32 and second portion 34. Although a particular configuration of stabilizer portion 20 and its portions 32, 34, 36 with respect to blade portion 20 is primarily described, the present invention contemplates stabilizer portion 20 having any suitable configuration with respect to blade portion 20. Stabilizer portion 20 cooperates with blade portion 16 to define an opening 38. Similar to apertures 30 of blade portion 16, opening 38 may channel the debris away from the tooth as the IER or other procedure is being performed.

As described above, in certain embodiments apparatus 10 includes a one-piece integrally-formed body 14 that envelops or otherwise covers appropriate portions of frame 12. In particular embodiments, body 14 may be formed plastic, including thermoplastic material, such as for example a composite thermoplastic material. The plastic forming body 14 may include a mostly synthetic or semi-synthetic organic condensation or polymerization product that may be molded or extruded in the desired form. In particular embodiments, body 14 may be formed of glass-fiber reinforced thermoplastic material, including material formed from a combination of semi-crystalline polyamide with partially aromatic copolyamide (e.g. GRIVORY GV-5 FA NATURAL made and sold by GRIVORY EMS of Germany). Such materials may provide advantageous properties for body 14, including, for example, high stiffness, strength, durability, stability, and/or chemical resistance.

Body 14 may be produced by a polymerization process that includes melting the polymer, placing frame 12 into a mold of the desired shape of body 14, allowing the melted polymer to envelop or otherwise cover appropriate portions of frame 12 inside the mold, and allowing the polymer to cool and harden to form body 14.

In certain embodiments, body 14 may fully or partially envelop or otherwise cover tang portion 18 and stabilizer portion 20, leaving at least a portion of abrasive surface 26 of blade portion 16 exposed. Additionally, the molding of body 14 around frame 12 may operate to couple body 14 to frame 12. In certain embodiments, frame 12 may include one or more apertures 40 through tang portion 18 and stabilizer portion 20. During the formation of body 14, the material forming body 14 may be allowed to flow through apertures 40 to improve the coupling of body 14 to frame 12. Although apertures 40 may facilitate the coupling of body 14 and frame 12, other suitable coupling mechanisms may additionally or alternatively couple body 14 to frame 12. For example, one or more rivets, screws, bolts, or other coupling mechanisms may couple body 14 to frame 12.

In certain embodiments, handle 42 includes a notch portion 44. Handle 42 may be understood to have at least two regions described in further detail below, a proximal region 46 and a distal region 48 that includes notch portion 44. Notch portion 44 may be formed at the same time using the polymerization process described above. In certain embodiments, notch portion 44 may be formed by removing material from handle 42 in order to create notch portion 44.

In certain embodiments, handle 42 may be gripped manually or mechanically by a clinical professional to perform TER or any other suitable procedure. An orthodontist or other clinical professional may use handle 42 to manually position apparatus 10 proximate the interproximal contact area of a person's tooth. As a result, the clinical professional using apparatus 10 may supply and control the force and motion necessary to advance abrasive surface 26 of blade portion 16 in opposing directions against the tooth.

Figure 1B:
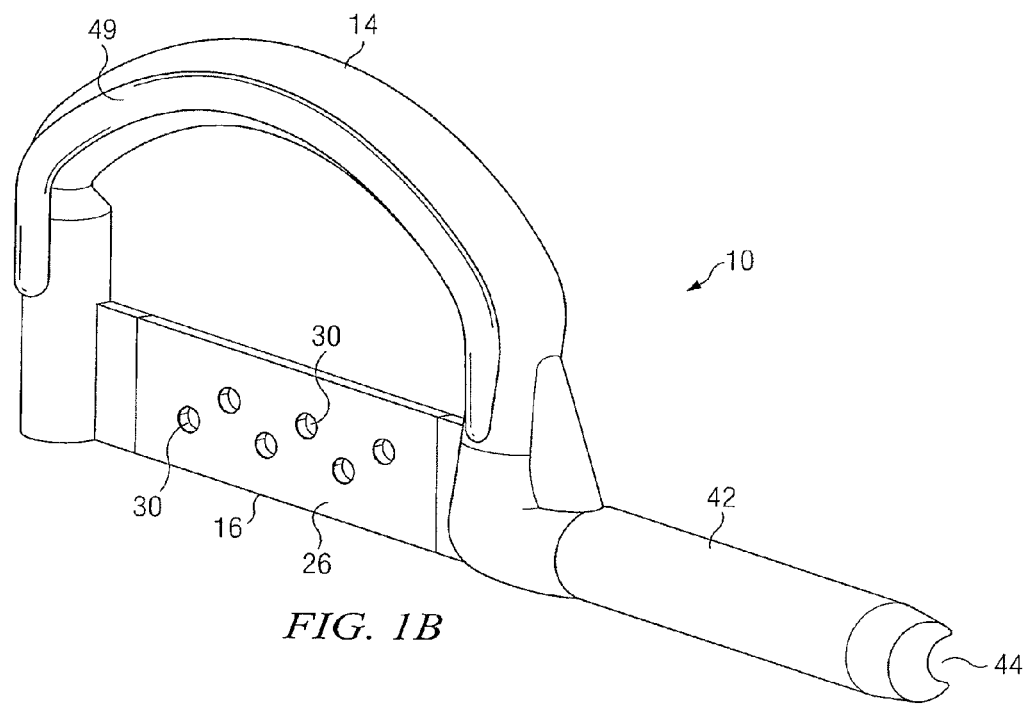
FIGS. 1B and 1C illustrate two views of the example apparatus from FIG. 1A with a fully formed body.
Figure 1C:
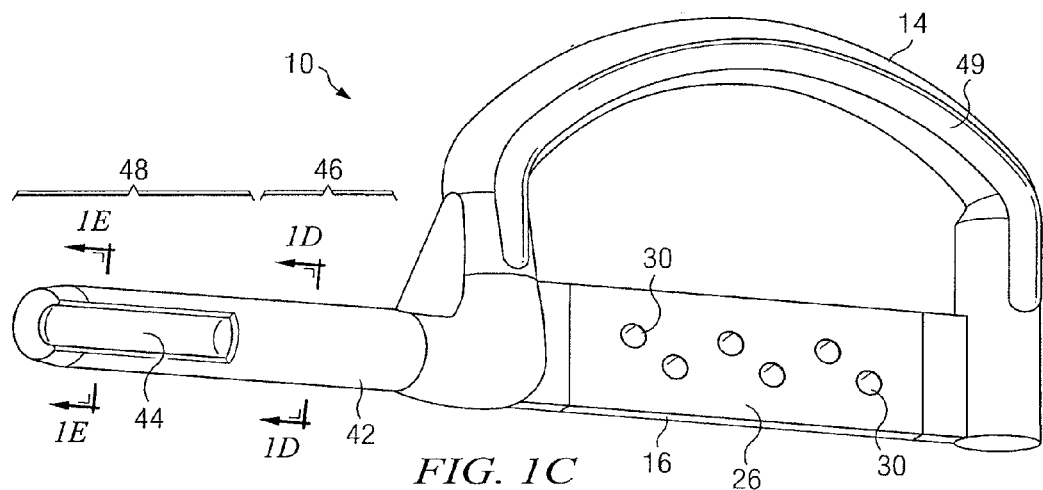

FIGS. 1B and 1C illustrate two views of an example apparatus 10 from FIG. 1A with a fully formed body 14. FIG. 1B illustrates an embodiment where stiffener 49 is provided. Stiffener 49 is coupled to body 14 and acts as additional structural support for body 14 in order to create additional stability and/or prevent breakage of stabilizer portion 20. Stiffener 49 may be formed using the plastic molding or extrusion method described above or via any other suitable method.

In FIG. 1C, example apparatus 10 is illustrated with blade portion 16 containing abrasive surface 26 and apertures 30. In the embodiment shown, handle 42 includes a proximal region 46 and a distal region 48. Proximal region 46, nearer to blade portion 16, has a substantially solid circular cross-section. This cross-section is described in greater detail in relation to FIG. 1D. Distal region 48, further from blade portion 16 includes notched region 44. Distal region 48 may have a substantially solid cross-section that is at least substantially semi-circular in shape. This cross-section is described in greater detail in FIG. 1E. Example alternative cross-sections are described in relation to FIGS. 1F-1J. Tang portion 18 may extend from proximal region 46 into distal region 48 that includes notched region 44.

Figure 1D:
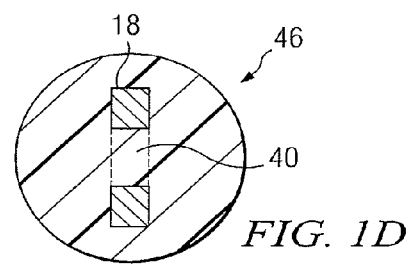
FIG. 1D illustrates an example cross-section of proximal region of the handle.

FIG. 1D illustrates an example cross-section of proximal region 46 of handle 42. In the embodiment shown, the perimeter of the cross-section is substantially circular and continuous. Tang portion 18 is enveloped by body 14. Body 14 may also have enveloped or flowed through the space created by apertures 30. In the illustrated example, the cross-section is substantially solid and comprises tang portion 18, which may be made of a metal, and body 14, which may have been formed using, for example, one of the polymerization methods described above.

Figure 1E:
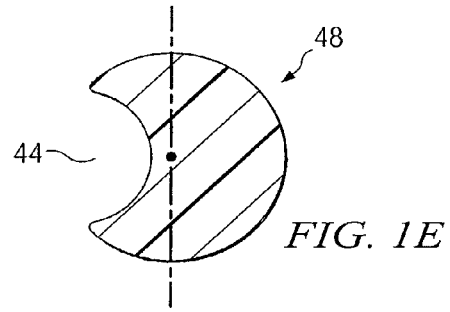
FIG. 1E illustrates an example cross-section of the distal region of the handle.

FIG. 1E illustrates an example cross-section of the distal region 48 of FIG. 1C. The cross-section is of at least a substantially semi-circular shape. This particular illustrated cross-section of distal region 48 has a perimeter with a first portion that defines approximately three-quarters of a circle with the radius of handle 42 and a second portion corresponding to notched region 44 that defines an arc with a radius that is less than the radius of handle 42. Further examples of cross-sections of the distal region 48 of FIG. 1C are illustrated below.

Figure 1F:
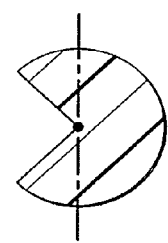
FIGS. 1F through 1J illustrate additional example alternative cross-sections of distal region.
Figure 1G:
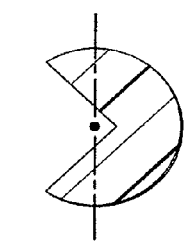
Figure 1H:
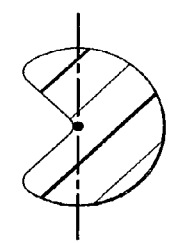
Figure 1I:
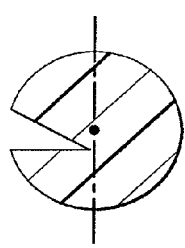
Figure 1J:
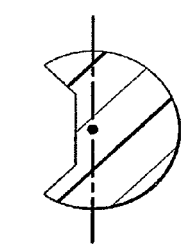

FIGS. 1F-1J illustrate additional example alternative cross-sections of distal region 48. FIG. 1F illustrates a cross-section where notched region 44 is defined by a 90 degree wedge that extends to the center of substantially circular perimeter of the cross-section of distal region 48. FIG. 1G illustrates a cross-section where notched region 44 is defined by a 90 degree wedge that extends slightly beyond the center of the substantially circular perimeter the cross-section of distal region 48. FIG. 1H illustrates a cross-section where notched region 44 is defined by a 90 degree wedge where the corners and the point of the wedge have a rounded shape. FIG. 1I illustrates a cross-section where notched region 44 is defined by a 30 degree wedge that does not extend fully to the center of the substantially circular shape defined by handle 42. FIG. 1J illustrates a cross-section where notched region is defined by an open trapezoidal shape. Accordingly, notched region 44 may be of any appropriate shape including shapes that do are not polygonal in nature.

Figure 2A:
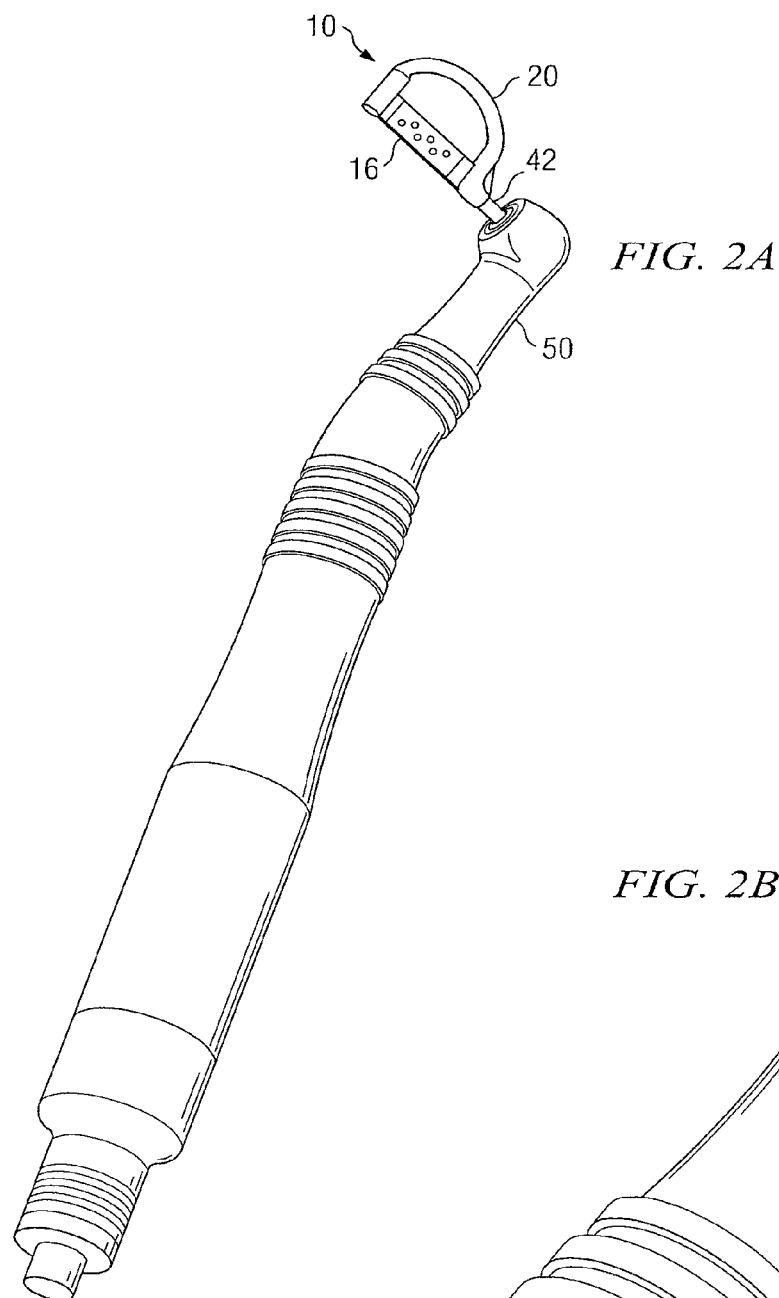
FIGS. 2A and 2B illustrate an example driver mechanism configured to couple to an example apparatus for removing enamel.
Figure 2B:
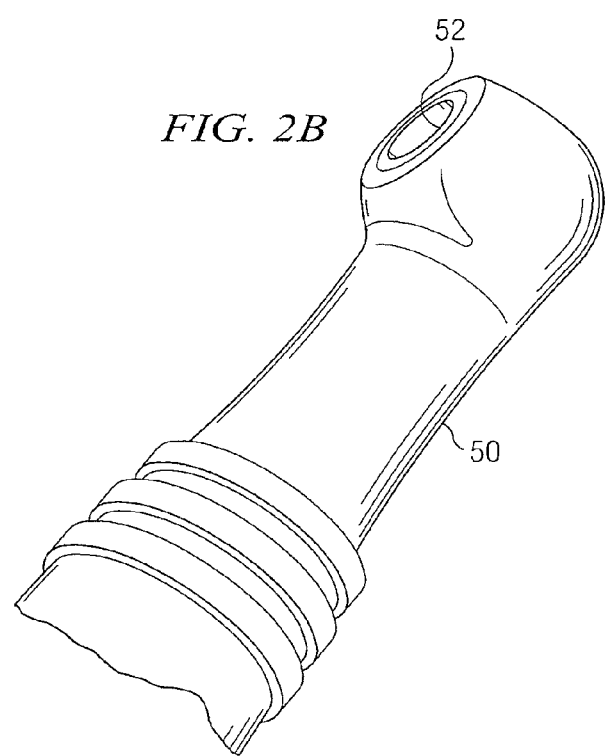

Regardless of the shape of the cross-section, distal region 48 may be adapted to use a compression fit into a driver mechanism as illustrated in FIGS. 2A and 2B. A compression fit may be achieved by using a slightly flexible material for all or a portion of handle 42. Distal region 48 may compress slightly or flex inward as it is inserted into a driver mechanism 50. The material then returns to its normal state to create the compression fit in driver mechanism 50. In certain embodiments the perimeter of the cross section of distal region 48 may define a circular arc in the range from 180 degrees to 330 degrees.

Additionally, although handle 42 has been illustrated with two distinct regions, additional regions may be provided without departing from the scope of the invention. For example, an intermediate region between proximal region 46 and distal region 48 could be provided. Further, although distal region 48 has been illustrated with a uniform cross-section, distal region 48 could have a non-uniform cross-section. For example, notched region 44 could taper as it approaches proximal region 46.

In certain embodiments, handle 42 may be configured to coupled to a driver mechanism. FIGS. 2A and 2B illustrate an example driver mechanism 50 adapted to couple to an example apparatus 10 for removing enamel from a person's tooth. Driver mechanism 50 may include a recess 52 adapted to receive and secure handle 42. For example, handle 42 may be force fitted into recess 52. As another example, handle 42 may be inserted into recess 52 and secured using a set screw or otherwise. Driver mechanism 50 may be operable to mechanically advance abrasive surface 26 in opposing directions against the tooth. As an example, driver mechanism 50 may be operable to mechanically move abrasive surface 26 in a substantially linear reciprocating motion. As another example, driver mechanism 50 may be operable to mechanically move abrasive surface 26 in a substantially elliptical reciprocating motion, with the elliptical path being in a plane substantially parallel to abrasive surface 26. For example, driver mechanism 50 may translate rotational movements, such as in a conventional dental drill, to reciprocating movements through appropriate gearing or other mechanisms. Such gearing or other mechanisms are well known to persons in the art. In certain embodiments, driver mechanism 50 may be configured to interchangeably receive and secure apparatus 10 and also other tools used in orthodontic or other clinical procedures. For example, driver mechanism 50 may be configured to also receive and secure a drill, polishing brush, or other tool.

In certain embodiments, handle 42 has at least two distinct regions, a proximal region 46 with a substantially circular cross-section with a substantially continuous circumference and a distal region 48 that includes notched region 44. The material of distal region 48 may compress slightly or flex inward as it is inserted into a driver mechanism 50. The material then returns to its normal state to create the compression fit in the driver mechanism. As a result, handle 42 may be fitted to into or otherwise coupled to recess 52 of driver mechanism 50 using a compression fit. As shown in FIGS. 1A, 1B, and 1C, handle 42 may have two regions that are substantially solid in cross-section including a portion of frame 12 covered by a portion of body 14. Alternatively, handle 42 may be formed solely by a portion of frame 12 or a metal, plastic, or other component coupled to frame 12. These embodiments may be distinguished from tools formed from molded sheet metal having thin-walled handles with C-shaped cross-sections. Such handles may be compressed and permanently or temporarily deformed when force-fitted into recess 52 of driver mechanism 50. Such deformation often results in permanent changes to the cross-sectional dimensions that may prevent the tools from properly and securely coupling to driver mechanism 50, especially after a number of uses. After repeated uses, such deformation may lead to material fatigue and, ultimately, failure.

Figure 3A:
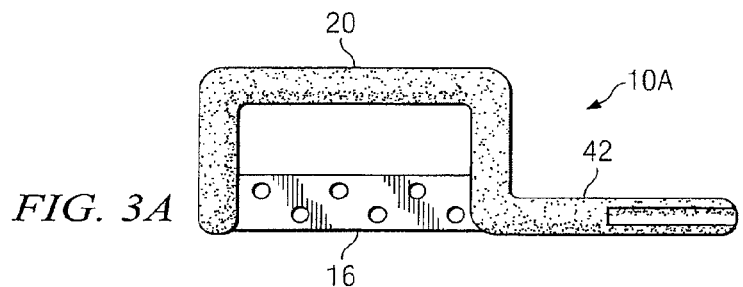
FIGS. 3A-3E illustrate examples of an apparatus for removing enamel from a person's tooth.
Figure 3B:
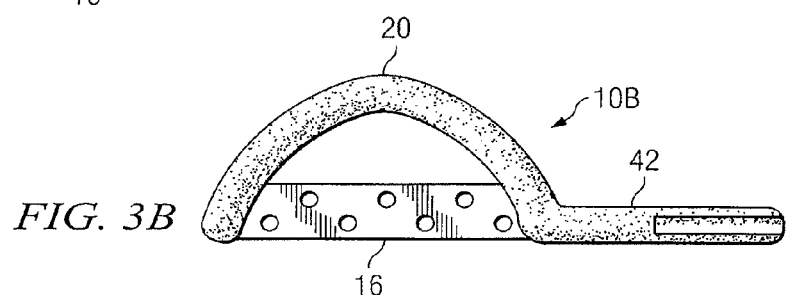
Figure 3C:
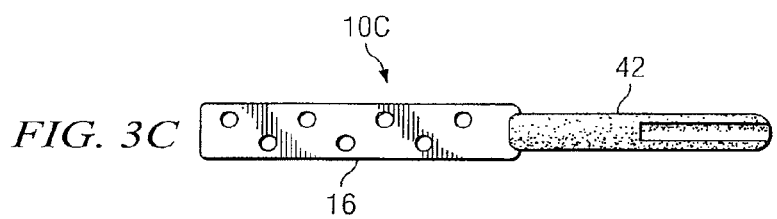
Figure 3D:
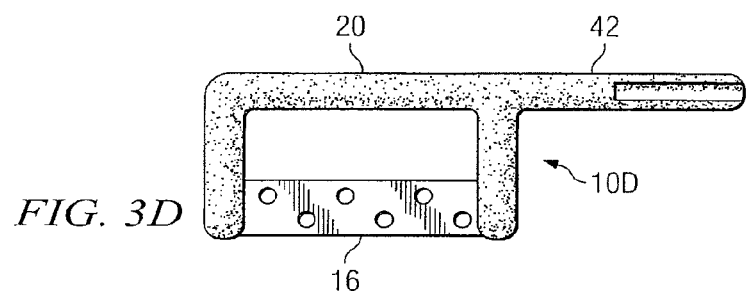
Figure 3E:
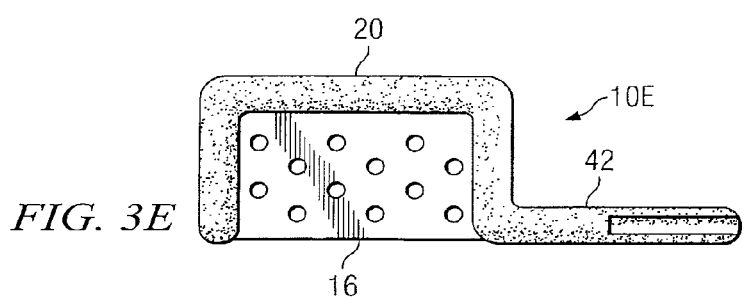

In certain embodiments, stabilizer portion 20 may be formed in a shape other than the shape illustrated in FIGS. 1A and 3A. FIGS. 3A-3E illustrate examples of alternative configurations of apparatus 10. As shown in FIG. 3A, in certain embodiments, stabilizer portion 20 may be substantially rectangular and formed by two posts that are perpendicular to blade portion with a third portion joining the two posts. As shown in FIG. 3B, stabilizer portion may be formed in the shape of an arc. As shown in FIG. 3C, in certain embodiments, apparatus 10 may be formed without stabilizer portion 20. As shown in FIG. 3D, in certain embodiments, handle 42 may extend from stabilizer portion 20. Although not shown, in certain embodiments, apparatus 10 may include multiple blade portions 16. For example, apparatus 10 may include first and second blade portions 16 offset in opposite directions from an axis through the length of handle 42. In any of these embodiments, blade portion 16 may be oriented relative to handle 42 at any suitable angle, including angles greater than or equal to zero degrees. As shown in FIG. 3E, in certain embodiments, blade portion 16 may extend to substantially fill the area defined by stabilizer portion 20.

Figure 4A:
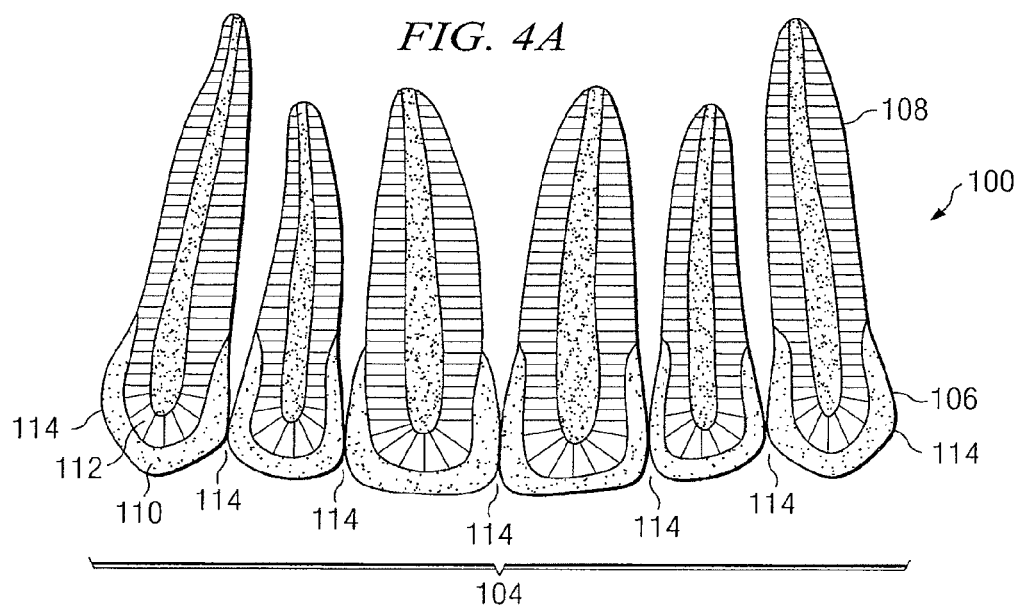
FIGS. 4A and 4B illustrate example upper and lower arches of a person's mouth and example interproximal contact areas from which enamel may be removed.
Figure 4B:
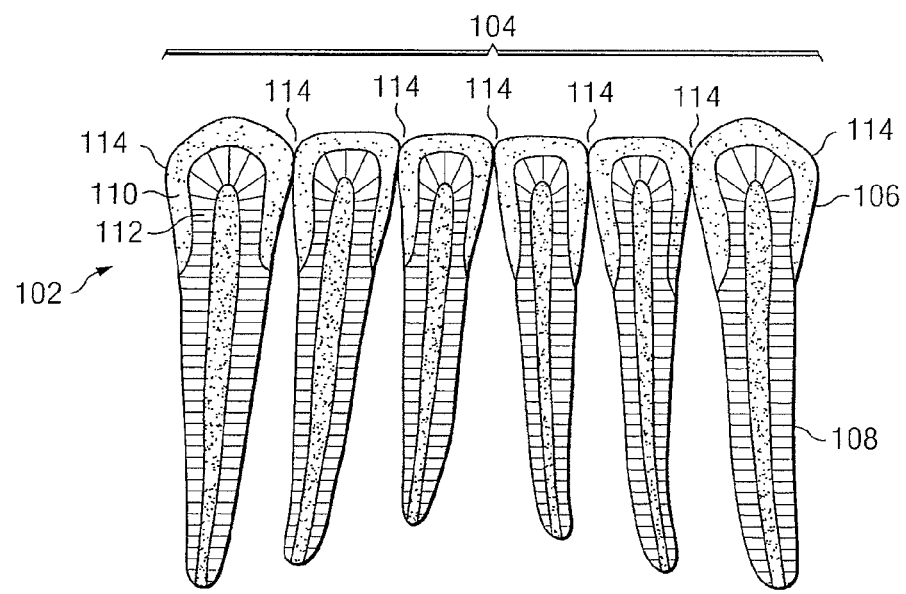

FIGS. 4A and 4B illustrate example upper and lower arches of a person's mouth and example interproximal contact areas from which enamel may be removed. FIG. 3A illustrates a portion of an example upper arch 100, and FIG. 4B illustrates a portion of an example lower arch 102. Upper arch 100 and lower arch 102 include anterior teeth 104. Each tooth 104 includes a protruding portion 106 and a root portion 108. Protruding portion 106 at least partially protrudes from the gum tissue covering the mandible. Root portion 108 extends into the mandible and secures tooth 104 in place.

Tooth 104 includes at least two layers. Enamel 110 forms an outer layer of tooth 104 and is comprised of a hard calcareous substance. An inner layer 112 is comprised of dentin and is very sensitive to decay, disease, and temperature. As described above, however, portions of enamel 110 may be removed from one or more interproximal contact areas 114 using an IER procedure. The removal of portions of enamel 110 from interproximal contact areas 114 may create space, or additional space, between two adjacent teeth 104. Accordingly, the IER procedure may be performed to prevent or treat the overcrowding of teeth 104 associated with malocclusion and avoid the need for tooth extractions. The IER procedure may also be used to recontour one or more teeth 104 to provide a more aesthetically pleasing shape. After portions of enamel 110 are removed at interproximal contact areas 114, teeth 104 may be polished and a protective treatment applied.

Because enamel 110 is a protective layer important to the structure and function of tooth 104, the amount of enamel 110 that may be removed during the IER procedure must be carefully controlled. In certain embodiments, approximately 0.85 mm to approximately 1.13 mm of enamel 110 may be safely removed from each interproximal area 114 of upper arch 100 without producing chronic sensitivity or pain. For example, approximately 1.13, 1.10, 0.91, 0.85, 0.91, 1.10, and 1.13 mm of enamel 110 may be removed from interproximal contact areas 114$a$-$g$, respectively. As a result, five medial spaces may be created at interproximal contact areas 114$b$-$f$, and a total of approximately 4.87 mm of medial space may be created. If enamel 110 at interproximal contact areas 114$a$ and 114$g$ is also reduced, the total medial space created in upper arch 100 may be approximately 7.13 mm. In certain embodiments, approximately 0.75 mm to approximately 1.00 mm of enamel 110 may be safely removed from each interproximal area 114 of lower arch 102 without producing chronic sensitivity or pain. For example, approximately 1.00, 0.82, 0.75, 0.75, 0.75, 0.82, and 1.00 mm of enamel 110 may be removed from interproximal contact areas 114$h$-$n$, respectively. As a result, five medial spaces may also be created at interproximal contact areas 114$i$-$n$, and a total of approximately 3.89 mm of medial space may be created. If enamel 110 at interproximal contact areas 114$h$ and 114$n$ is also reduced, the total medial space created in lower arch 102 may be approximately 5.89 mm.

Figure 5:
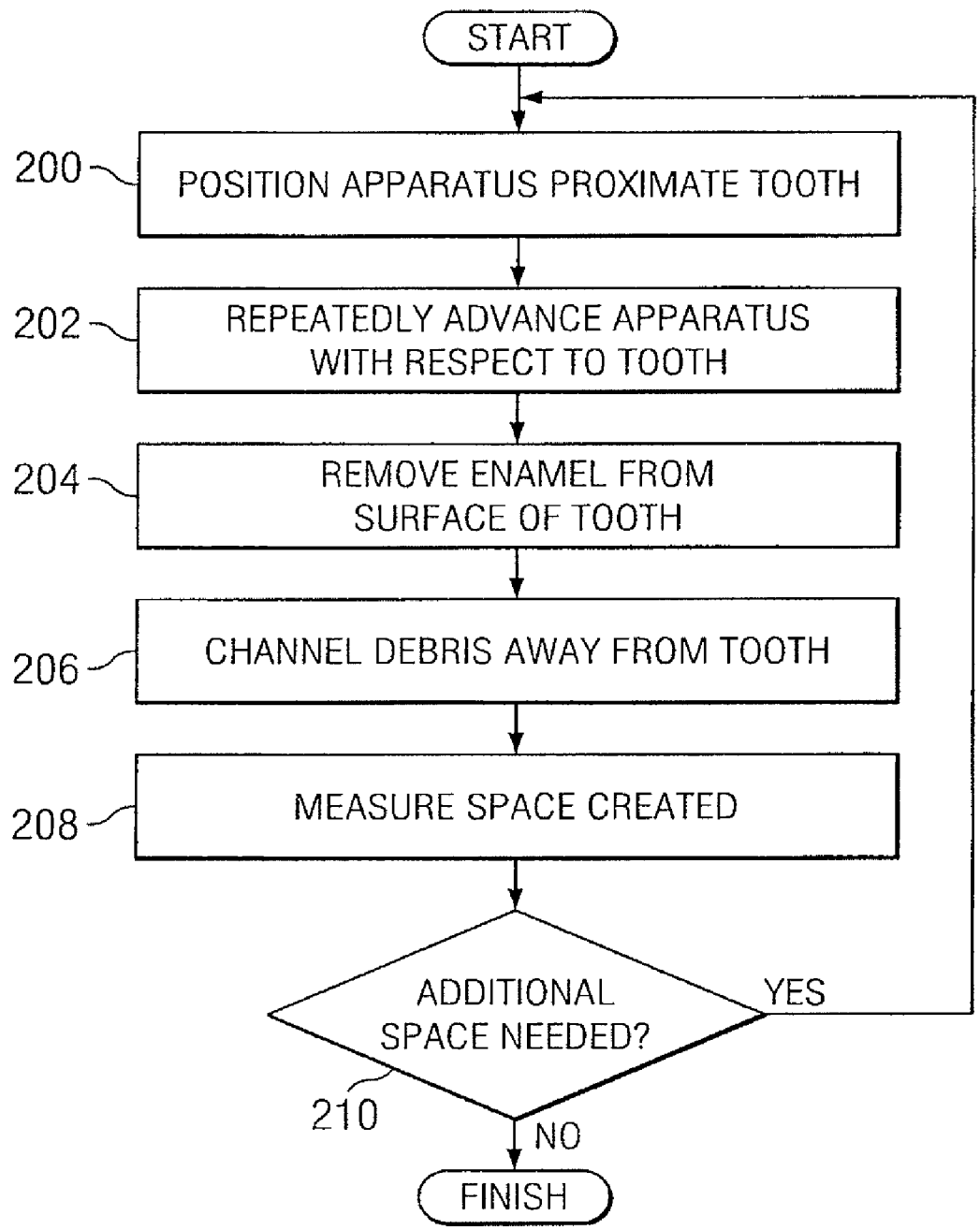
FIG. 5 illustrates an example method for removing enamel from a person's tooth.

FIG. 5 illustrates an example method for removing enamel from a person's tooth 104. The method may include some or all of an IER procedure. At step 200, apparatus 10 is positioned proximate a particular tooth 104 of a person's upper or lower arch 100 or 102. Specifically, abrasive surface 26 may be positioned proximate an interproximal contact area 114 of tooth 104. At step 202, apparatus 10 is repeatedly advanced in opposing directions with respect to tooth 104. Apparatus 10 may be advanced in opposing directions with respect to tooth 104 in a first direction towards the labial surface of tooth 104 and in a second direction towards the lingual surface of tooth 104. As a result, at step 204, abrasive surface 26 may file, saw, or otherwise remove enamel 110 from tooth 104. Enamel 110 may be removed in a similar manner from an adjacent tooth 104. As a result of enamel 110 being removed from one or both adjacent teeth 104, a space or additional space is created between adjacent teeth 104 to prevent or treat overcrowding of teeth 104 associated with malocclusion and avoid the need for tooth extractions. Alternatively or additionally, enamel 110 may be removed from tooth 104 to provide a more aesthetically pleasing shape.

At step 206, as enamel 110 is removed from tooth 104, in certain embodiments debris is channeled away from tooth 104 through one or more apertures 30 formed through blade portion 16 of frame 12. The debris present at interproximal area 114 may include, for example, bits of removed enamel, saliva, blood, and any liquids, chemicals or pastes used in the IER procedure. As a result, such debris may be readily removed from the interproximal area and the area kept cleaner and visibly unobstructed during an IER procedure, without undue interruption.

At step 208, the space created between adjacent teeth 104 is measured. The amount of space to be created depends on the amount of overcrowding, the desired shape and size of the tooth, and other factors particular to the person. At step 210, the clinical professional determines whether additional space is needed. If additional space is needed, the method returns to step 200 for removal of additional enamel 110. The method may continue by repeating steps 200-210 on the same tooth 104 or on an adjacent tooth 104 until the desired amount of space is created. When it is determined at step 210 that additional space is not needed, the method ends.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for removing enamel from a person's tooth to create additional space in the person's mouth to treat or prevent malocclusion, to recontour the tooth to create a more aesthetically pleasing shape, or to treat any other condition that may be improved through the reshaping or resizing of the person's tooth.

Although the present invention has been described above in connection with several embodiments, changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. An apparatus for removing enamel from a person's tooth, comprising:
    a blade portion comprising an abrasive surface adapted to remove enamel from the tooth in response to reciprocating movement of the abrasive surface against the enamel of the tooth; and
    a handle portion coupled to the blade portion, the handle portion comprising a region having a substantially solid cross-section with at least a substantially semi-circular perimeter, the substantially solid cross-section defining a notched region;
    wherein the notched region defines an open shape that allows the length of the handle portion to flex inward when inserted into a corresponding opening in a driver mechanism, creating a compression fit in the driver mechanism.

2. The apparatus of claim 1, wherein the apparatus is configured to be inserted via a pressure fit into a corresponding opening in a driver mechanism configured to drive reciprocating movement of the blade portion to provide the reciprocating movement of the abrasive surface.

3. The apparatus of claim 1, wherein the blade portion comprises one or more apertures formed through the blade portion and adapted to channel away from the tooth debris resulting from the removal of enamel from the tooth.

4. The apparatus of claim 1, wherein the substantially solid cross-section is defined by a perimeter in the shape of a substantially circular arc establishing at least 180 degrees and no more than 330 degrees of a circle.

5. The apparatus of claim 1, wherein the substantially solid cross-section is defined by a perimeter in the shape of a substantially circular arc establishing approximately 270 degrees of a circle.

6. The apparatus of claim 1, wherein the abrasive surface comprises diamond dust.

7. The apparatus of claim 1, wherein at least a portion of the handle comprises stainless steel.

8. The apparatus of claim 1, wherein the apparatus comprises a body coupled to a frame by a polymerization product that covers portions of the frame.

9. The apparatus of claim 1, wherein the apparatus comprises a body, wherein the body comprises a glass-fiber reinforced thermoplastic material.

10. The apparatus of claim 1, wherein the apparatus comprises a body, wherein the body comprises a material formed from a combination of semi-crystalline polyamide with partially aromatic copolyamide.

11. An apparatus for removing enamel from a person's tooth, comprising:
    a driver mechanism;
    a tool adapted to removably couple to the driver mechanism, the tool comprising:
        a blade portion comprising:
            an abrasive surface extending between two edges of the blade portion and adapted to remove enamel from the tooth in response to reciprocating movement of the abrasive surface against the enamel of the tooth; and
            one or more apertures formed through the blade portion and adapted to channel away from the tooth debris resulting from the removal of enamel from the tooth; and
        a handle portion coupled to the blade portion, the handle portion comprising a region having a substantially solid cross-section with at least a substantially semi-circular perimeter, the substantially solid cross-section defining a notched region;
    wherein the notched region defines an open shape that allows the handle portion to flex inward when inserted into a corresponding opening in the driver mechanism, creating a compression fit in the driver mechanism.

12. The apparatus of claim 11, wherein the handle portion comprises a glass-fiber reinforced thermoplastic material.

13. The apparatus of claim 11, wherein the handle portion comprises a material formed from a combination of semi-crystalline polyamide with partially aromatic copolyamide.

14. A method for removing enamel from a person's tooth, comprising:
    positioning an apparatus for removing enamel proximate the tooth, the apparatus comprising:
        a blade portion comprising an abrasive surface adapted to remove enamel from the tooth in response to reciprocating movement of the abrasive surface against the enamel of the tooth; and
        a handle portion coupled to the blade portion, the handle portion comprising a region having a substantially solid cross-section with at least a substantially semi-circular perimeter, the substantially solid cross-section defining a notched region, wherein the notched region defines an open shape that allows the handle portion to flex inward when inserted into a corresponding opening in a driver mechanism, creating a compression fit in the driver mechanism;

moving the abrasive surface of the blade portion against the enamel of the tooth in a reciprocating motion; and removing enamel from the tooth in response to the reciprocating movement of the abrasive surface of the blade portion against the enamel of the tooth.

15. The method of claim 14, wherein the substantially solid cross-section is defined by a perimeter in the shape of a substantially circular arc establishing at least 180 degrees and no more than 330 degrees of a circle.

16. The method of claim 14, wherein the substantially solid cross-section is defined by a perimeter in the shape of a substantially circular arc establishing approximately 270 degrees of a circle.

17. The method of claim 14, wherein the blade portion comprises one or more apertures formed through the blade portion and adapted to channel away from the tooth debris resulting from the removal of enamel from the tooth.

18. The method of claim 14, wherein the abrasive surface comprises diamond dust.

19. The method of claim 14, wherein the handle portion comprises stainless steel.

20. The method of claim 14, wherein the handle portion comprises glass-fiber reinforced thermoplastic material.

21. The method of claim 14, wherein the handle portion comprises a material formed from a combination of semi-crystalline polyamide with partially aromatic copolyamide.

22. The method for claim 14, wherein: the positioning the apparatus for removing enamel and the moving the abrasive surface are preformed using the driver mechanism, the driver mechanism adapted to drive reciprocating movement of the blade portion to provide the reciprocating movement of the abrasive surface.

* * * * *